(12) United States Patent
Levine et al.

(10) Patent No.: US 8,150,516 B2
(45) Date of Patent: Apr. 3, 2012

(54) SYSTEMS AND METHODS FOR OPERATING AN IMPLANTABLE DEVICE FOR MEDICAL PROCEDURES

(75) Inventors: Paul A. Levine, Santa Clarita, CA (US); Eliot L. Ostrow, Sunnyvale, CA (US)

(73) Assignee: Pacesetter, Inc., Sylmar, CA (US)

( * ) Notice: Subject to any disclaimer, the term of this patent is extended or adjusted under 35 U.S.C. 154(b) by 605 days.

(21) Appl. No.: 12/332,768

(22) Filed: Dec. 11, 2008

(65) Prior Publication Data

US 2010/0152806 A1   Jun. 17, 2010

(51) Int. Cl.
*A61N 1/00* (2006.01)
(52) U.S. Cl. ......................................................... 607/30
(58) Field of Classification Search ............. 340/539.11; 600/423; 604/500; 607/2, 11, 30, 31, 32, 607/60

See application file for complete search history.

(56) References Cited

U.S. PATENT DOCUMENTS

| | | | |
|---|---|---|---|
| 4,788,980 A | 12/1988 | Mann et al. | |
| 4,940,052 A | 7/1990 | Mann et al. | |
| 6,129,746 A | 10/2000 | Levine et al. | |
| 6,243,606 B1 | 6/2001 | Mann et al. | |
| 6,259,950 B1 | 7/2001 | Mann et al. | |
| 6,263,244 B1 | 7/2001 | Mann et al. | |
| 6,285,908 B1 | 9/2001 | Mann et al. | |
| 6,295,471 B1 | 9/2001 | Bornzin et al. | |
| 6,311,089 B1 | 10/2001 | Mann et al. | |
| 6,366,812 B1 | 4/2002 | Levine et al. | |
| 6,389,316 B1 | 5/2002 | Bornzin et al. | |
| 6,408,210 B1 | 6/2002 | Bornzin et al. | |
| 6,430,441 B1 | 8/2002 | Levine | |
| 6,477,417 B1 | 11/2002 | Levine | |
| 6,546,288 B1 | 4/2003 | Levine | |
| 6,584,354 B1 | 6/2003 | Mann et al. | |
| 6,594,523 B1 | 7/2003 | Levine | |
| 6,618,622 B1 | 9/2003 | Mann et al. | |
| 6,721,601 B1 | 4/2004 | Bornzin et al. | |
| 6,766,197 B1 | 7/2004 | Levine | |
| 6,792,307 B1 | 9/2004 | Levine et al. | |
| 6,925,326 B1 | 8/2005 | Levine et al. | |
| 6,934,587 B1 | 8/2005 | Bornzin et al. | |
| 7,031,773 B1 | 4/2006 | Levine et al. | |
| 8,014,867 B2 * | 9/2011 | Cooke et al. | 607/31 |
| 2006/0293591 A1 * | 12/2006 | Wahlstrand et al. | 600/423 |
| 2009/0138058 A1 | 5/2009 | Cooke et al. | |
| 2009/0157146 A1 * | 6/2009 | Linder et al. | 607/60 |
| 2009/0163980 A1 | 6/2009 | Stevenson | |
| 2010/0152806 A1 | 6/2010 | Levine et al. | |

OTHER PUBLICATIONS

Sullivan, Roberta RN, BSN, MPH et al., "Prevent life-threatening communication breakdowns," Nursing. 2008;38(2):17.

* cited by examiner

*Primary Examiner* — George Manuel
*Assistant Examiner* — Robert Wieland

(57) ABSTRACT

When a medical procedure is performed on a patient in whom an implantable medical device is implanted, the medical procedure may have undesired effects on the medical device, such as triggering a response that initiates therapy by the device that is unnecessary and potentially dangerous to the patient. Systems and methods may facilitate performing of such medical procedures on such patients by temporarily reprogramming the medical device, monitoring for one or more detectable characteristics associated with the medical procedure to be performed, and restoring normal programming of the device based on detection and/or lack of detection of the detectable characteristic(s).

20 Claims, 7 Drawing Sheets

SYSTEMS AND METHODS FOR OPERATING AN IMPLANTABLE DEVICE FOR MEDICAL PROCEDURES

FIELD OF THE INVENTION

The present invention relates to medical devices and methods. More specifically, the present invention relates to implantable medical devices and methods of operating such devices, particularly for performing medical procedures not associated with such devices.

BACKGROUND OF THE INVENTION

Implantable cardiac devices have become increasingly sophisticated and more capable over time. The initial implantable cardiac devices were typically comprised of pacemakers, which provided electrical pacing pulses to the heart at a generally fixed rate. As the technology has developed, more advanced pacing systems have been implanted in patients, which, for example, are capable of providing pacing pulses to the heart only when the pacing system determines that the heart will not provide an intrinsic heart beat. Moreover, such advanced pacemakers are also able to adjust the pacing rate to accommodate different levels of physical activity and corresponding metabolic demand of the patient.

Typically, pacing systems are equipped with sensors, which provide signals that are used by the control unit of the pacing system to determine the pacing rate. Such sensors include activity sensors, such as an accelerometer, metabolic rate sensors, such as a minute ventilation sensor, electrical sensors, such as an impedance sensor, and pressure sensors.

Cardiac devices are also known to be able to perform automatic testing functions, such as threshold testing for automatic capture verification. Examples of known devices and methods include those described in U.S. Pat. Nos. 6,129,746; 6,243,606; 6,259,950; 6,263,244; 6,285,908; 6,295,471; 6,311,089; 6,366,812; 6,389,316; 6,408,210; 6,430,441; 6,477,417; 6,546,288; 6,584,354; 6,594,523; 6,618,622; 6,721,601; 6,766,197; 6,792,307; 6,925,326; and 6,934,587, each of which is incorporated by reference herein in its entirety.

Further, some cardiac devices are known to include lead impedance surveillance capabilities. For example, U.S. Pat. No. 7,031,773 to Levine et al., which is incorporated by reference herein in its entirety, describes a system in which an impedance measurement is triggered by a high capture threshold identified by an automatic capture algorithm.

BRIEF SUMMARY

Once a device is implanted in a patient, the device is typically not removed, absent a need to repair or replace the device. Thus, when the patient undergoes a medical procedure involving magnetic and/or electric fields, voltage and/or current signals, or other electrical and/or magnetic effects, the device may be subjected to such effects. The patient should be protected from the device misinterpreting the effects of the medical procedure to trigger a response, such as pacing therapy, for example, in the case of a cardiac device. In general, the patient should be protected from an implantable device delivering inappropriate therapy as a result of the medical procedure. For example, strong fluctuating magnetic fields associated with magnetic resonance imaging (MRI) may be seen as rapid signals and misinterpreted by an implantable cardiac device to trigger pacing therapy. In the patient who is not actually in need of pacing therapy, the mis-triggered pacing therapy may pose a significant risk to the patient. Thus, the device should be rendered compatible with the medical procedure to be performed, not only by structural design features but also via operational features.

One approach is to have a doctor or medical technician specifically program the device prior to the medical procedure to inhibit the device from delivering therapy in response to the medical procedure. After the medical procedure is completed, the doctor or medical technician must reprogram the device to the pre-procedure or normal settings. As used herein, the term normal is intended to encompass non-medical procedure conditions and operating parameters that correspond to non-medical procedure conditions.

Alternatively, embodiments described herein contemplate temporarily altering at least one operating parameter of an implantable device prior to a medical procedure and automatically returning the at least one operating parameter to a pre-procedure setting after the medical procedure is completed. In such embodiments, the doctor or medical technician may not be required after the medical procedure is completed to reprogram the device.

Embodiments described herein also contemplate automatically temporarily altering the at least one operating parameter upon initiation of the medical procedure. In such embodiments, the doctor of medical technician may be able to set at least one interim operating parameter to be implemented automatically upon initiation of the medical procedure, so that the medical device operates normally until the medical procedure begins. Thus, the patient may be protected by normal operation of the medical device and is not subject to the interim operating parameter until the medical procedure begins.

Embodiments described herein contemplate a method for operating a medical device for facilitating a medical procedure, particularly where the medical device is implanted in a patient. The method may include: storing at least one normal operating parameter of the device in a storage element of the device; setting at least one interim operating parameter for the device; monitoring for at least one detectable characteristic of the medical procedure to be performed on the patient; and based upon detection of the at least one detectable characteristic, retrieving the at least one normal operating parameter from the storage element and replacing the at least one interim operating parameter with the retrieved at least one normal operating parameter. This approach may allow the medical device to automatically return to normal operation once the medical procedure is completed, for example, a certain time after a last detection of the detectable characteristic of the medical procedure occurs.

In some embodiments, the method may include storing the at least one interim parameter in the storage element of the device, and the setting of the at least one interim operating parameter may be based upon detection of the at least one detectable characteristic. This approach may allow the medical device to operate using the at least one normal operating parameter until the beginning of the medical procedure is detected, and then switch to the at least one interim operating parameter during the medical procedure. Thus, in such embodiments, the patient may automatically receive the benefit of normal operation of the medical device before and after the medical procedure, with the interim operating parameter(s) being used only during the period in which the detectable characteristic of the medical procedure is detected.

In some embodiments, the method may also include determining the at least one detectable characteristic based on the medical procedure to be performed.

In some embodiments, the method may include identifying the medical procedure to be performed to the device. In such embodiments, the device may automatically determine the at least one detectable characteristic to monitor based on the identified medical procedure. Alternatively, the device may provide a list of medical procedures, and identifying the medical procedure to be performed may include selecting a procedure from the list. In such embodiments, the device may automatically determine the at least one detectable characteristic to monitor based on the selected procedure.

In some embodiments, the at least one interim operating parameter may be set based on the medical procedure to be performed.

In some embodiments, the method may include identifying the medical procedure to be performed to the device. In such embodiments, the device may automatically set the at least one interim operating parameter based on the identified medical procedure. Alternatively, the device may provide a list of medical procedures, and identifying the medical procedure to be performed may include selecting a procedure from the list. In such embodiments, the device may automatically set the at least one interim operating parameter based on the selected procedure.

In some embodiments, the device may automatically retrieve the at least one normal operating parameter from the storage element and replace the at least one interim operating parameter with the retrieved at least one normal operating parameter based on detection of the at least one detectable characteristic. In such embodiments, retrieving the at least one normal operating parameter from the storage element and replacing the at least one interim operating parameter with the retrieved at least one normal operating parameter may occur at a predetermined elapsed time after detection of the at least one detectable characteristic. Alternatively or additionally, the retrieving and replacing may occur at the predetermined elapsed time after a last detection of the at least one detectable characteristic.

In some embodiments, the monitoring may be performed by the device.

Embodiments described herein contemplate a method for operating a medical device for facilitating a medical procedure, particularly where the medical device is implanted in a patient. The method may include: storing at least one normal operating parameter of the device in a storage element of the device; setting at least one interim operating parameter for the device; setting a first period of time; during the first set period of time, monitoring for at least one detectable characteristic of a medical procedure to be performed on the patient; and when the at least one detectable characteristic is not detected during the first set period of time, retrieving the at least one normal operating parameter from the storage element and replacing the at least one interim operating parameter with the retrieved at least one normal operating parameter.

In some embodiments, the method may include: storing the at least one interim operating parameter in the storage element of the device, and the setting of the at least one interim operating parameter may be based on detection of the at least one detectable characteristic during the first set period of time. In such embodiments, the setting of the at least one interim operating parameter may occur upon detection of the at least one detectable characteristic during the first set period of time.

In some embodiments, the method may include: setting a second period of time; and when the at least one detectable characteristic is detected during the first set period of time, retrieving the at least one normal operating parameter from the storage element and replacing the at least one interim operating parameter with the retrieved at least one normal operating parameter at an end of the second set period of time after detection of the at least one detectable characteristic. Alternatively or additionally, the retrieving and replacing may be at the end of the second set period of time after a last detection of the at least one detectable characteristic.

Embodiments described herein contemplate a method for operating a medical device for facilitating a medical procedure, particularly where the medical device is implanted in a patient. The method may include: altering at least one operating parameter of the device from a pre-procedure setting; monitoring for at least one detectable characteristic of a medical procedure to be performed on the patient; and returning the at least one operating parameter to the pre-procedure setting based upon detection of the at least one detectable characteristic.

In some embodiments, the altering of at least one parameter from the pre-procedure setting may be based upon detection of the at least one detectable characteristic.

In some embodiments, the method may include identifying the medical procedure to be performed on the patient to the device. In such embodiments, the method may include altering the at least one operating parameter from the pre-procedure setting based on the identified medical procedure. In such embodiments, the device may automatically alter the at least one operating parameter from the pre-procedure setting based on the identified medical procedure.

Alternatively or additionally, the method may include determining the at least one detectable characteristic based on the identified medical procedure. In such embodiments, the device may automatically determine the at least one detectable characteristic based on the identified medical procedure.

In some embodiments, the device may automatically return the at least one operating parameter to the pre-procedure setting based on detection of the at least one detectable characteristic. In such embodiments, the method may include returning the at least one operating parameter to the pre-procedure setting at a predetermined elapsed time after detection of the at least one detectable characteristic. Alternatively or additionally, the returning may occur at the predetermined elapsed time after a last detection of the at least one detectable characteristic.

In some embodiments, the monitoring may be performed by the device.

Embodiments described herein contemplate a method for operating a medical device for facilitating a medical procedure, particularly where the medical device is implanted in a patient. The method may include: altering at least one operating parameter of the device from a pre-procedure setting; setting a first period of time; during the first set period of time, monitoring for at least one detectable characteristic of a medical procedure to be performed on the patient; and when the at least one detectable characteristic is not detected during the first set period of time, returning the at least one operating parameter to the pre-procedure setting.

In some embodiments, the altering of the at least one operating parameter from the pre-procedure setting may be based on detection of the at least one detectable characteristic during the first set period of time. In such embodiments, the altering of the at least one operating parameter from the pre-procedure setting may occur upon detection of the at least one detectable characteristic during the first set period of time.

In some embodiments, the method may include: setting a second period of time; and when the at least one detectable characteristic is detected during the first set period of time, returning the at least one operating parameter to the pre-procedure setting at an end of the second set period of time after detection of the at least one detectable characteristic. Alternatively or additionally, the returning may occur at the end of the second set period of time after a last detection of the at least one detectable characteristic.

Embodiments described herein contemplate a system for operating an implantable medical device. The system may include: an implantable medical device; a storage element; and a processor. The processor may be configured to: store at least one normal operating parameter for the device in the storage element; set at least one interim operating parameter for the device; monitor for at least one detectable characteristic of a medical procedure to be performed; and, based on detection of the at least one detectable characteristic, retrieve the at least one normal operating parameter from the storage element and replace the at least one interim operating parameter with the retrieved at least one normal operating parameter.

In some embodiments, the processor may be configured to store the at least one interim operating parameter and to set the at least one interim operating parameter for the device based on detection of the at least one detectable characteristic. In such embodiments, the processor may be configured to set the at least one interim operating parameter for the device upon detection of the at least one detectable characteristic.

In some embodiments, the system may include a user interface coupled to the processor and configured to receive user input to identify the medical procedure to be performed. In such embodiments, the processor may be configured to automatically determine the at least one detectable characteristic based on the medical procedure identified by the user input. Alternatively or additionally, the processor may be configured to automatically determine the at least one interim operating parameter based on the medical procedure identified by the user input. Alternatively or additionally, the user interface may be configured to receive user input to set the at least one interim operating parameter. Alternatively or additionally, the user interface may be configured to receive user input to determine the at least one detectable characteristic.

In some embodiments, the processor may be configured to retrieve the at least one normal operating parameter from the storage element and replace the at least one interim operating parameter with the retrieved at least one normal operating parameter at a predetermined elapsed time after detection of the at least one detectable characteristic. Alternatively or additionally, the processor may be configured to retrieve the at least one normal operating parameter from the storage element and replace the at least one interim operating parameter with the retrieved at least one normal operating parameter at a predetermined elapsed time after a last detection of the at least one detectable characteristic.

In any of such embodiments, the systems may include a user interface coupled to the processor and configured to receive user input to determine the elapsed time. Alternatively or additionally, the system may include a user interface coupled to the processor and configured to receive user input to identify the medical procedure to be performed, wherein the processor is configured to automatically determine the elapsed time based on the medical procedure identified by the user input. The user may also be able to set or select a total duration of the elapsed time during which the at least one interim operating parameter is in effect until being replaced by the at least one normal operating parameter.

Embodiments described herein contemplate a system for operating an implantable medical device. The system may include: an implantable medical device; a storage element; and a processor. The processor may be configured to store at least one normal operating parameter for the device in the storage element; set at least one interim operating parameter for the device; set a first period of time; monitor, during the first set period of time, for at least one detectable characteristic of a medical procedure to be performed; and, when the at least one detectable characteristic is not detected during the first set period of time, retrieve the at least one normal operating parameter from the storage element and replace the at least one interim operating parameter with the retrieved at least one normal operating parameter.

In some embodiments, the processor may be configured to store the at least one interim operating parameter in the storage element of the device and set the at least one interim operating parameter based on detection of the at least one detectable characteristic during the first set period of time. In such embodiments, the processor may be configured to set the at least one interim operating parameter upon detection of the at least one detectable characteristic during the first set period of time.

In some embodiments, the system may include a user interface coupled to the processor and configured to receive user input to set the first period of time. Alternatively or additionally, the system may include a user interface coupled to the processor and configured to receive user input to identify the medical procedure to be performed, wherein the processor is configured to automatically set the first period of time based on the medical procedure identified by the user input.

In some embodiments, the processor may further be configured to: set a second period of time; and, when the at least one detectable characteristic is detected during the first set period of time, retrieve the at least one normal operating parameter from the storage element and replace the at least one interim operating parameter with the retrieved at least one normal operating parameter at an end of the second set period of time after detection of the at least one detectable characteristic. Alternatively or additionally, the processor may be configured to, when the at least one detectable characteristic is detected during the first set period of time, retrieve the at least one normal operating parameter from the storage element and replace the at least one interim operating parameter with the retrieved at least one normal operating parameter at the end of the second set period of time after a last detection of the at least one detectable characteristic.

In any of such embodiments, the system may include a user interface coupled to the processor and configured to receive user input to set the second period of time. Alternatively or additionally, the system may include a user interface coupled to the processor and configured to receive user input to identify the medical procedure to be performed, wherein the processor is configured to automatically set the second period of time based on the medical procedure identified by the user input.

Embodiments described herein contemplate a system for operating an implantable medical device. The system may include: an implantable medical device; and a processor. The processor may be configured to: alter at least one operating parameter of the device from a pre-procedure setting; monitor for at least one detectable characteristic of a medical procedure to be performed on the patient; and return the at least one operating parameter to the pre-procedure setting based upon detection of the at least one detectable characteristic.

In some embodiments, the processor may be configured to alter the at least one operating parameter from the pre-procedure setting based on detection of the at least one detectable characteristic during the first set period of time. In such embodiments, the processor may be configured to alter the at least one operating parameter from the pre-procedure setting upon detection of the at least one detectable characteristic during the first set period of time.

In some embodiments, the system may include a user interface coupled to the processor and configured to receive user input to identify the medical procedure to be performed. In such embodiments, the processor may be configured to automatically determine the at least one detectable characteristic based on the medical procedure identified by the user input. Alternatively or additionally, the processor may be configured to automatically alter the at least one operating parameter from the pre-procedure setting based on the medical procedure identified by the user input. Alternatively or additionally, the user interface may be configured to receive user input to alter the at least one operating parameter from the pre-procedure setting. Alternatively or additionally, the user interface may be configured to receive user input to determine the at least one detectable characteristic.

In some embodiments, the processor may be configured to return the at least one operating parameter to the pre-procedure setting at a predetermined elapsed time after detection of the at least one detectable characteristic. Alternatively or additionally, the processor may be configured to return the at least one operating parameter to the pre-procedure setting at a predetermined elapsed time after a last detection of the at least one detectable characteristic.

In any of such embodiments, the system may include a user interface coupled to the processor and configured to receive user input to determine the elapsed time. Alternatively or additionally, the system may include a user interface coupled to the processor and configured to receive user input to identify the medical procedure to be performed, wherein the processor is configured to automatically determine the elapsed time based on the medical procedure identified by the user input.

Embodiments described herein contemplate a system for operating an implantable medical device. The system may include: an implantable medical device; and a processor. The processor may be configured to: alter at least one operating parameter of the device from a pre-procedure setting; set a first period of time; during the first set period of time, monitor for at least one detectable characteristic of a medical procedure to be performed; and, when the at least one detectable characteristic is not detected during the first set period of time, return the at least one operating parameter to the pre-procedure setting.

In some embodiments, the processor may be configured to alter the at least one operating parameter from the pre-procedure setting based on detection of the at least one detectable characteristic during the first set period of time. In such embodiments, the processor may be configured to alter the at least one operating parameter from the pre-procedure setting upon detection of the at least one detectable characteristic during the first set period of time.

In some embodiments, the system may include a user interface coupled to the processor and configured to receive user input to set the first period of time. Alternatively or additionally, the system may include a user interface coupled to the processor and configured to receive user input to identify the medical procedure to be performed, wherein the processor is configured to automatically set the first period of time based on the medical procedure identified by the user input.

In some embodiments, the processor may be configured to: set a second period of time; and, when the at least one detectable characteristic is detected during the first set period of time, return the at least one operating parameter to the pre-procedure setting at an end of the second set period of time after detection of the at least one detectable characteristic. Alternatively or additionally, the processor may be configured to return the at least one operating parameter to the pre-procedure setting at the end of the second set period of time after a last detection of the at least one detectable characteristic.

In any of such embodiments, the system may include a user interface coupled to the processor and configured to receive user input to set the second period of time. Alternatively or additionally, the system may include a user interface coupled to the processor and configured to receive user input to identify the medical procedure to be performed, wherein the processor is configured to automatically set the second period of time based on the medical procedure identified by the user input.

While multiple embodiments are disclosed, still other embodiments will become apparent to those skilled in the art form the following detailed description, which shows and describes illustrative embodiments. As will be realized, the details provided herein are capable of modifications in various aspects, all without departing form the spirit and scope of the present invention. Accordingly, the drawings and detailed description are to be regarded as illustrative in nature and not restrictive.

DETAILED DESCRIPTION

Figure 1:
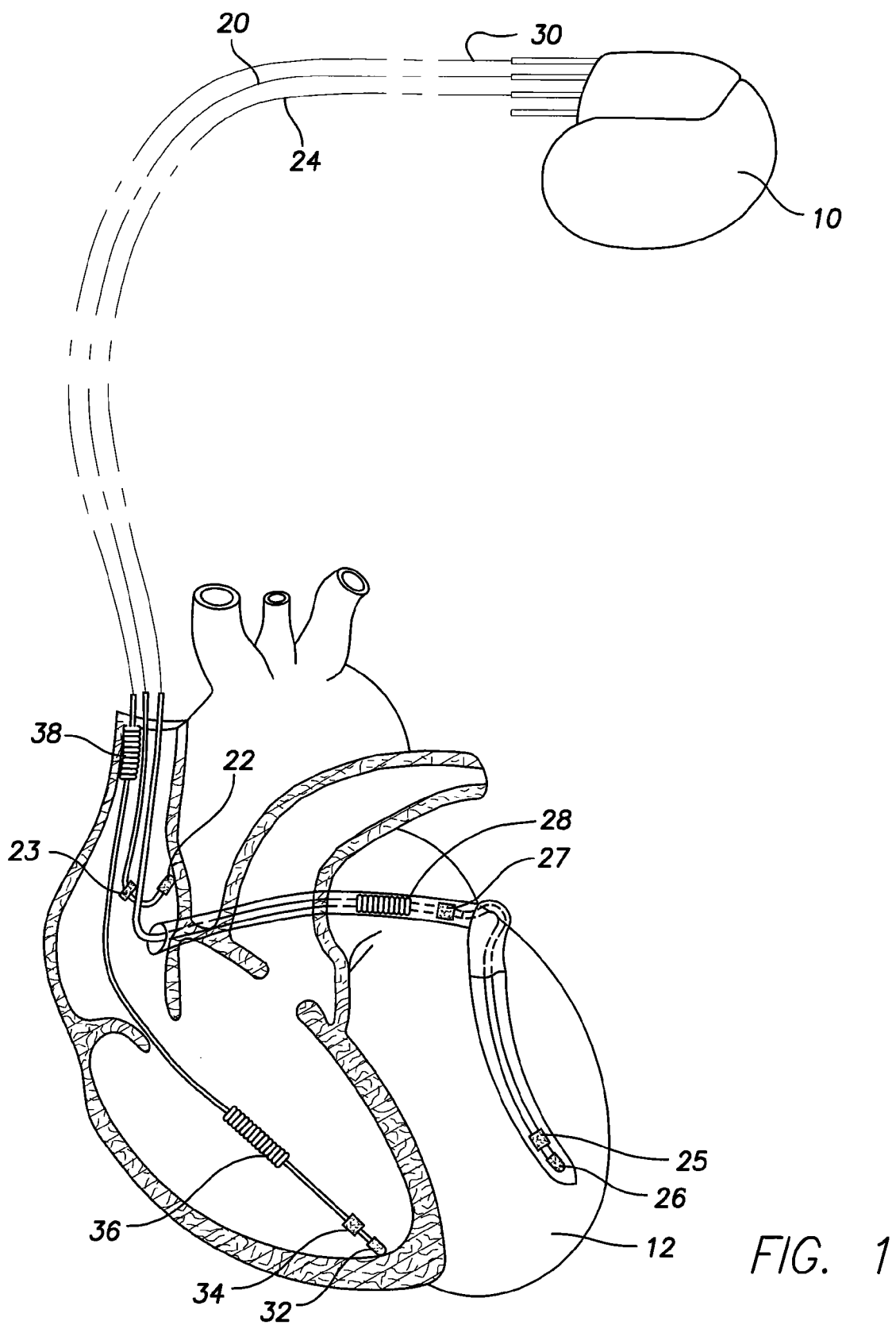
FIG. 1 is a simplified, partly cutaway view of a patient's heart and illustrating an implantable stimulation device in electrical communication with at least three leads implanted into the heart for delivering multi-chamber stimulation and shock therapy.

The following description is of embodiments presently contemplated for practicing various aspects of the invention. This description is not to be taken in a limiting sense but is made merely for the purpose of describing general principles. The scope of the invention should be ascertained with reference to the issued claims. In the description that follows, like numerals or reference designators will be used to refer to like parts or elements throughout.

Embodiments are described herein in relation to a cardiac stimulation device capable of delivering precisely ordered stimulation pulses to multiple chambers of the heart, referred to herein as multi-chamber stimulation, or to multiple sites within a chamber of the heart, referred to herein as multi-site stimulation. It should be understood, however, that the systems and methods described herein may be applied to simpler devices, such as single or dual chamber stimulation devices, as well as entirely different medical devices that may be subject to interference of complications during medical procedures.

The stimulation device illustrated, by way of example, is intended for use in patients suffering from hemodynamic dysfunction, which may or may not be accompanied by conduction disorders. Precisely controlled stimulation at multiple sites or in multiple chambers is provided to intentionally make use of the pacing function of the heart to improve cardiac hemodynamics by re-coordinating heart chamber contractions and/or preventing arrhythmogenic depolarizations from occurring. Thus, the cardiac stimulation device is capable of delivering at least low-voltage stimulation pulses to multiple stimulation sites for providing pacing therapy, and may include high-voltage stimulation shocks for providing cardioversion therapy and defibrillation therapy.

The disclosed systems and methods are directed at operating an implantable medical device. In particular, the disclosed devices and methods are described with respect to operating an implantable cardiac device, although the types of implantable medical devices with which the systems and methods disclosed herein are not limited as such. In general, the systems and methods disclosed herein may find application for implantable medical devices that may need to be temporarily reprogrammed to facilitate performing a medical procedure.

As discussed above, when a medical procedure is performed on a patient in whom an implantable medical device is implanted, the medical procedure may have undesired effects on the medical device, such as triggering a response that initiates therapy by the device that is unnecessary and potentially dangerous to the patient. The types of medical procedures may include, but are not limited to, magnetic resonance imaging (MRI), surgery involving electrocautery, electroconvulsive therapy, or any other procedure, whether therapeutic or diagnostic, that produces electrical and/or magnetic fields, voltages, currents, or other signals that may interfere with or otherwise affect operation of an implantable medical device. As the types of implantable medical devices contemplated are not limited, it should be understood that the medical procedures that may be accounted for or otherwise facilitated by the systems and methods described herein are also not limited.

Embodiments described herein may provide enhanced safety to the patient during various medical procedures by reprogramming the implantable medical device to implement interim (e.g., temporary) operating parameters to reduce its susceptibility to the effects of the various medical procedures. Further, embodiments described herein may provide enhanced safety to the patient and/or convenience to the patient and/or medical staff by providing an automated return to normal programming, for example, to avoid undesirable periods in which the medical device programmed to the interim operating parameters and thus not subject to its normal programming. As used herein, normal programming is meant to encompass programming of the device that allows the device to provide the intended medical benefits of the device. As such, normal programming is intended to encompass all programming of the device that is desired during conventional use of the particular device, including any programming specific to activities, such as exercise or rest, or modes, such as diagnostic or monitoring, as opposed to interim programming that renders the device set up for one specific capability or rendering the device less susceptible to the effect(s) of a particular medical procedure to be performed, which, without the interim programming, would otherwise reduce or impair the ability of the medical device to perform its intended functions.

The interim programming may alter one or more thresholds for triggering operation of the device, for example. Alternatively or additionally, the interim programming may disable one or more functions of the device. As such, returning the device to its normal programming may include resetting the threshold(s) to a value that is within a range of values as determined for normal operation of the device and/or enabling the function(s) disabled by the interim programming. It should be understood that the interim programming suitable may vary based on the particular medical device and/or the particular medical procedure to be performed, and similarly the normal programming may vary based on the particular medical device.

For example, an implantable cardioverter defibrillator (ICD) may be provided with programming that disables tachyarrhythmia therapy and/or pacing therapy. For example, for pacing in a patient with high grade AV block, it would be appropriate to protect the patient from oversensing the fluctuating magnetic fields produced during MRI. Thus, it may be appropriate to inhibit the normal operation of the ICD by programming the ICD to an asynchronous mode with no sensing, potentially setting the basic rate of the device to a higher rate than the patient's intrinsic rhythm to minimize competition, and also potentially at higher outputs to address concerns with an increase in capture thresholds during the MRI procedure. As known in the art, burns or damage to the electrode-cardiac tissue interface caused by MRI may increase the amount of energy needed for effective pacing. Thus, the output being delivered from the pulse generator to the lead may be increased to provide an added safety margin. If no increase is identified by post-procedure evaluation, the output may be reduced. As such burns or damage may also attenuate the intrinsic signals (complexes) arising from the patient, it may be desirable to make the ICD more sensitive, that is, able to recognize smaller signals.

In particular, by programming the ICD to the a medical procedure compatible mode (e.g., OOO, ODO, or XOO modes as defined by the generic pacemaker code (NGB code)), all special algorithms that provide various functions and operations to deal with specific cardiac conditions and/or situations (such as, but not limited to, AutoCapture, Ventricular Intrinsic Preference, Rate Modulation, Rate Responsive AV Delay and Rest Rate) will be disabled and will need to be restored after the MRI procedure is completed. With respect to an ICD capable of delivering both pacing therapy and tachyarrhythmia therapy, it may be appropriate to disable both by altering the programming of parameters particular to each. However, the availability of knowledgeable medical staff to restore such programming may prevent a timely restoration. Further, if the MRI procedure is provided as an outpatient service, the patient may have to return to a different medical facility for reprogramming of the device.

Throughout this disclosure, the programming is discussed in terms of operating parameters. The term "operating parameters" is intended to encompass any setting, value, mode, or other feature of a medical device that affects or is otherwise involved with its operation. Although some operating parameters may not be subject to change or programming, it should be understood that only operating parameters that may be changed or programmed may be involved in the systems and methods described herein.

In one embodiment, a method for operating a medical device for facilitating a medical procedure, particularly where the medical device is implanted in a patient, may involve storing at least one current or normal operating parameter of the device in a storage element of the device and setting at least one interim operating parameter for the device.

The normal operating parameter may correspond normal programming, as discussed above, and the interim operating parameter may correspond to interim programming that facilitates performing the medical procedure safely, for example, with reduced interference with and/or effect on the medical device during the procedure.

The method may also include monitoring, during the procedure, for at least one detectable characteristic of the particular medical procedure. The detectable characteristic may be any suitable characteristic associated with the medical procedure, such as an effect, field, signal, or the like. For example, a detectable characteristic for MRI may be a strong magnetic field and/or fluctuations in a magnetic field. For electrocautery, a detectable characteristic may be an electric current or voltage, or a signal within a particular frequency range. Other detectable characteristics may include, but are not limited to, electric fields, radiation (e.g., radiation therapy), and the like. In general, any characteristic associated with or produced by performing a particular medical procedure may be monitored, particularly any characteristic that involves exposure to the medical device, and thus may be detected by the medical device during performance of the procedure. Thus, it should be understood that the system may include any suitable sensors and/or detectors conventionally used to monitor and/or detect such characteristics, as well as any sensors hereafter developed to detect characteristics of known or later developed medical procedures.

Based upon detection of the at least one detectable characteristic, the at least one normal operating parameter may be retrieved from the storage element and the at least one interim operating parameter may be replaced with the retrieved at least one operating parameter. Detection of the at least one detectable characteristic may indicate that the medical procedure is being performed at a particular time, for example. Such knowledge may be used to determine an appropriate time to discontinue the interim programming and to resume normal programming for the medical device. Thus, the method may allow the medical device may be reprogrammed to interim operating parameter(s) to facilitate the safe performance of the medical device while the patient is undergoing the medical procedure, and then returned to normal programming (stored/retrieved normal operating parameter(s)) upon completion of the medical procedure.

Because there may be a variable time period between the time a doctor or medical technician prepares the patient for the medical procedure by reprogramming the medical device for the medical procedure and the start of the procedure, and/or a variable time period in which the medical procedure is performed (start to completion), the actual time that the medical procedure is performed and/or completed may provide an appropriate trigger or guide for safely reestablishing normal programming for the medical device.

However, it may be desirable to implement the interim operating parameters only once the medical procedure has begun, thus allowing the patient to receive the benefit of the normal operating parameters up until the medical procedure begins. Thus, the interim operating parameter(s) may be stored and then retrieved and implemented once the medical procedure is started.

The method may include determining the at least one detectable characteristic based on the medical procedure to be performed. As discussed above, different medical procedures may have different detectable characteristics. As such, rather than monitor for all possible characteristics, once the medical procedure to be performed is known, a particular detectable characteristic to be monitored may be determined.

In some embodiments, this may be a manual determination, that is, an operation performed by the doctor or medical technician interfacing with the medical device. For example, the doctor or medical technician may select or otherwise input a characteristic to be monitored to whatever device is to perform the monitoring. Alternatively or additionally, the doctor or medical technician may select or otherwise input a particular medical procedure to such device, and be presented with a list of characteristics to be monitored based on the particular medical procedure.

In some embodiments, the implantable medical device may perform the monitoring. Thus, in some embodiments, the method may include identifying the medical procedure to be performed to the device. The device may then automatically determine the at least one detectable characteristic to monitor based on the identified medical procedure, or may provide a list of characteristics for selection and/or input by a user. The medical device may provide a list of medical procedures so that the user may identify the medical procedure to be performed by include selecting a procedure from the list or alternatively entering a non-listed procedure. In some embodiments, the device may automatically determine the at least one detectable characteristic to monitor based on the selected procedure, for example, when the procedure is listed, and/or may provide one or more default characteristics to be monitored, for example, when the procedure is not listed.

Similarly, the at least one interim operating parameter may be set based on the medical procedure to be performed, either by the doctor or medical technician, or automatically by the medical device. Thus, the device itself may be configured to perform as much or as little of the method as appropriate or desired. For example, the doctor or medical technician may only select, input or otherwise communicate a medical procedure to be performed, and the medical device may automatically reprogram itself, monitor for one or more detectable characteristics for the particular medical procedure, and return itself to normal programming based upon detection of the detectable characteristic(s), such as after a predetermined time after the last detection, without further interaction by the doctor or medical technician, if desired.

In some embodiments, as opposed to automation of other operations, the device may automatically retrieve the at least one normal operating parameter from the storage element and replace the at least one interim operating parameter with the retrieved at least one normal operating parameter based on detection of the at least one detectable characteristic. In such embodiments, retrieving the at least one normal operating parameter from the storage element and replacing the at least one interim operating parameter with the retrieved at least one normal operating parameter may occur at a predetermined elapsed time after detection of the at least one detectable characteristic. The predetermined elapsed time may be sufficient to allow the medical procedure to be completed, for example, with a suitable margin for safety before the device is returned to normal programming. As such, the detection of the characteristic may be any detection, such as one of many possible detections, so long as the predetermined elapsed time properly accounts for the time that the medical procedure may take to complete.

Alternatively or additionally, the retrieving and replacing may occur at the predetermined elapsed time after a last detection of the at least one detectable characteristic. This may allow the completion of the medical procedure to be detected. Once a first detection of the characteristic is made, the medical device or other device monitoring for the characteristic may perform a monitoring algorithm that include monitoring an elapsed time between detections of the characteristic. By using a suitable elapsed time between detections, an end or completion of the medical procedure may be identified by a last detection of the characteristic, that is, a detection of the characteristic that is not followed by another detection of the characteristic within the elapsed time. This may allow the completion of the medical procedure to be identified with more certainty, and thus may allow a relatively shorter time period before restoring the normal programming of the device.

Other embodiments may provide a method for operating a medical device for facilitating a medical procedure that includes: storing at least one normal operating parameter of the device in a storage element of the device; setting at least one interim operating parameter for the device; and setting a first period of time. During the first set period of time, monitoring for at least one detectable characteristic of a medical procedure is performed. When the at least one detectable characteristic is not detected during the first set period of time, the at least one normal operating parameter may be retrieved from the storage element and the at least one interim operating parameter may be replaced with the retrieved at least one operating parameter. This method may, for example, provide enhanced safety for the patient by preventing the device from being reprogrammed for too long of a period of time without having the procedure performed.

Ideally, the device may be reprogrammed to facilitate a particular medical procedure and then be reset to normal programming after the procedure, either automatically or manually as a matter of a course of treatment. However, if the medical procedure is unduly delayed, either by a matter of hours or a matter of days, for example, the device would remain reprogrammed for an extended and/or unintended time period, which may place the patient at an unacceptable risk with the device not operating with normal programming for the extended/unintended time period. By setting a suitable first period of time, the method may provide a safe "window" or time period for the medical procedure to be performed. If the medical procedure is not performed within the first set period of time, the characteristic will not be detected during the first set period of time, and the device will be returned to normal programming, thus returning the patient to the health benefits provided by the device operating with normal programming.

Alternatively, the at least one interim operating parameter may be stored, and may only be set once the at least one characteristic is detected. Thus, the medical device may remain programmed with the at least one normal operating parameter until the medical procedure has begun, by detecting the detectable characteristic.

In some embodiments, the method may include setting a second period of time. When the at least one detectable characteristic is detected during the first set period of time, the at least one normal operating parameter may be retrieved from the storage element and the at least one interim operating parameter may be replaced with the retrieved at least one normal operating parameter at the second set period of time after detection of the at least one detectable characteristic. Setting the second period of time provides a basis to reestablish the normal programming for the device. As discussed above, the device may automatically return to normal programming based on detection of the characteristic(s). In this case, the device returns to normal programming at the second set period of time after detection. As discussed above, the detection may be any one of many detections, or alternatively may be a last detection of the characteristic.

In general, the first time period may be the time in which the medical procedure is expected to take place and the second time period may be the time within which the medical procedure is expected to be completed. However, such times may include safety margins and may be set as appropriate or desired.

It should be understood that the methods described above are only examples and that other embodiments are also contemplated. As such, it should be understood that different implementations may be envisioned with different operations that still effectuate methods for operating a medical device for facilitating a medical procedure. For example, as described herein, such a method may include: altering at least one operating parameter of the device from a pre-procedure setting; monitoring for at least one detectable characteristic of a medical procedure to be performed on the patient; and returning the at least one operating parameter to the pre-procedure setting based upon detection of the at least one detectable characteristic. Alternatively or additionally, such a method may include: altering at least one operating parameter of the device from a pre-procedure setting; setting a first period of time; during the first set period of time, monitoring for at least one detectable characteristic of a medical procedure to be performed on the patient; and when the at least one detectable characteristic is not detected during the first set period of time, returning the at least one operating parameter to the pre-procedure setting.

Alternatively, the method may include altering the at least one operating parameter of the device from the pre-procedure setting upon detection of the at least one detectable characteristic. As discussed above, this allows the normal programming to continue until the medical procedure begins.

Various embodiments described herein contemplate a system for operating an implantable medical device. The system may be implemented, either in part or entirely, by the medical device. Thus, it should be understood that the system, either in part or entirely, may be implanted in a patient. However, the disclosure provided herein is not intended to limit the implementation to a particular physical arrangement as various arrangements and configurations are possible and contemplated, as will be apparent from this disclosure.

In some embodiments, the system may include an implantable medical device, a storage element, and a processor. The processor may be configured to: store at least one normal operating parameter for the device in the storage element; set at least one interim operating parameter for the device; and monitor for at least one detectable characteristic of a medical procedure to be performed. Based on detection of the at least one detectable characteristic, the processor may be configured to retrieve the at least one normal operating parameter from the storage element and replace the at least one interim operating parameter with the retrieved at least one operating parameter. In some embodiments, the processor may be configured to retrieve the at least one normal operating parameter from the storage element and replace the at least one interim operating parameter with the retrieved at least one normal operating parameter at a predetermined elapsed time after detection of the at least one detectable characteristic and/or after a last detection of the at least one detectable characteristic.

Alternatively, the processor may be configured to store the at least one interim operating parameter, and to set the at least one interim operating parameter for the device upon detection of the at least one detectable characteristic.

It should be understood that the processor may be configured to perform such operations via other devices, elements and/or software, as appropriate or desired. However, the particular details of such devices, elements or software are not discussed herein as they would be amenable to numerous design choices as desired for a particular implementation, as would be apparent to those skilled in the art based on the disclosure provided herein.

In some embodiments, the system may include a user interface coupled to the processor and configured to receive user input to identify the medical procedure to be performed, to receive user input to set the at least one interim operating parameter, to determine the at least one detectable characteristic, and/or to determine an elapsed time. Based on the medical procedure identified by user input, the processor may be configured to automatically determine the at least one detectable characteristic, to automatically determine the at least one interim operating parameter, and/or to automatically determine the elapsed time.

Other embodiments of a system that include an implantable medical device, a storage element, and a processor may have the processor configured to: store at least one normal operating parameter for the device in the storage element; set at least one interim operating parameter for the device; and set a first period of time. The processor may further be configured to monitor, during the first set period of time, for at least one detectable characteristic of a medical procedure to be performed. When the at least one detectable characteristic is not detected during the first set period of time, the processor may retrieve the at least one normal operating parameter from the storage element and replace the at least one interim operating parameter with the retrieved at least one normal operating parameter.

Alternatively, the processor may be configured to store the at least one interim operating parameter for the device in the storage element, and to set at least one interim operating parameter for the device upon detection of the at least one detectable characteristic during the first set period of time.

In some embodiments, the processor may further be configured to set a second period of time. When the at least one detectable characteristic is detected during the first set period of time, the processor may retrieve the at least one normal operating parameter from the storage element and replace the at least one interim operating parameter with the retrieved at least one normal operating parameter at the second set period of time after detection of the at least one detectable characteristic, and/or after a last detection of the at least one detectable characteristic.

Similar to above, the system may include a user interface coupled to the processor and configured to receive user input to set the first period of time, to receive user input to identify the medical procedure to be performed, and/or to receive user input to set the second period of time.

Based on the medical procedure identified by the user input, the processor may be configured to automatically set the first period of time, and/or to automatically set the second period of time.

Other embodiments of a system for operating an implantable medical device may include an implantable medical device and a processor. The processor may be configured to: alter at least one operating parameter of the device from a pre-procedure setting; monitor for at least one detectable characteristic of a medical procedure to be performed on the patient; and return the at least one operating parameter to the pre-procedure setting based upon detection of the at least one detectable characteristic. Further, the processor may be configured to return the at least one operating parameter to the pre-procedure setting at a predetermined elapsed time after detection of the at least one detectable characteristic, and/or after a last detection of the at least one detectable characteristic. Alternatively or additionally, the processor may be configured to: alter at least one operating parameter of the device from a pre-procedure setting; set a first period of time; during the first set period of time, monitor for at least one detectable characteristic of a medical procedure to be performed; and, when the at least one detectable characteristic is not detected during the first set period of time, return the at least one operating parameter to the pre-procedure setting. Further, the processor may be configured to: set a second period of time; and, when the at least one detectable characteristic is detected during the first set period of time, return the at least one operating parameter to the pre-procedure setting at the second set period of time after detection of the at least one detectable characteristic, and/or after a last detection of the at least one detectable characteristic.

Similar to above, the system may include a user interface coupled to the processor and configured to receive user input to identify the medical procedure to be performed, to alter the at least one operating parameter, to determine the at least one detectable characteristic, to receive user input to determine the elapsed time, to receive user input to set the first period of time, and/or to receive user input to set the second period of time.

Similar to above, based on the medical procedure identified by the user input, the processor may be configured to automatically determine the at least one detectable characteristic, to automatically alter the at least one operating parameter from the pre-procedure setting, to automatically determine the elapsed time, to automatically set the first period of time, and/or to automatically set the second period of time.

It should be understood that such systems may be configured to implement corresponding methods discussed above. Thus, it should be understood that various features described herein with respect to particular embodiments of systems and/or methods may be combined with other embodiments of systems and/or methods, as appropriate or desired.

Figure 2:
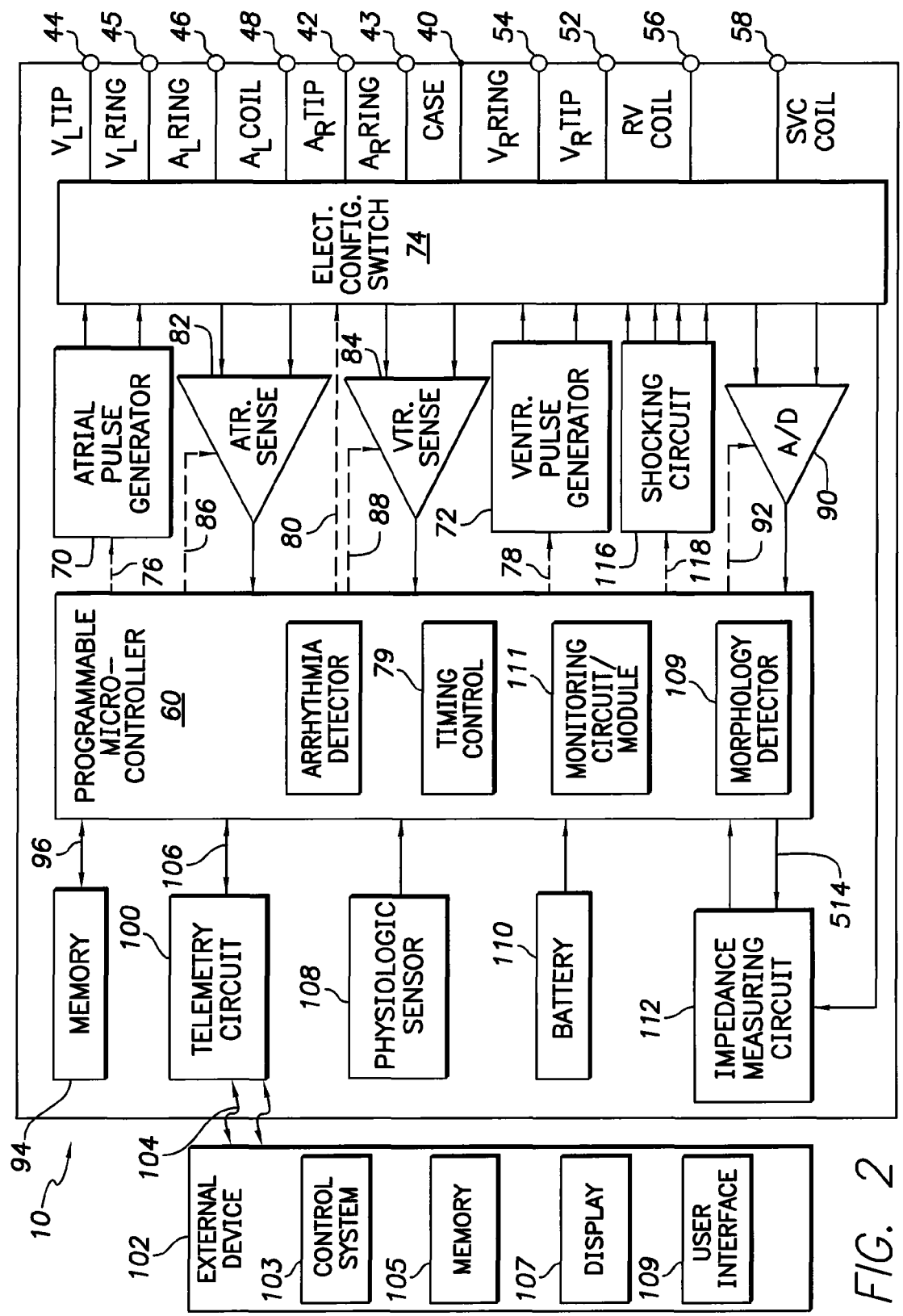
FIG. 2 is a functional block diagram of the multi-chamber implantable stimulation device of FIG. 1, illustrating the basic elements that provide pacing stimulation, cardioversion, and defibrillation in four chambers of the heart.

Turning now to a general cardiac stimulation device in which the methods described herein may be implemented or with which the systems described herein may be implemented, reference may be had to FIGS. 1 and 2. As discussed above, however, it should be understood that numerous variations exist of such a device in/with which the methods/systems may be implemented. Similarly, a general telemetry/programmer device is described in conjunction with FIG. 3. The telemetry/programmer device may be used to program and/or obtain data from the cardiac stimulation device. It should be understood, however, that numerous variations of telemetry/programmer devices exist that may be used.

FIG. 1 illustrates a stimulation device 10 in electrical communication with a patient's heart 12 by way of three leads 20, 24 and 30 suitable for delivering multi-chamber stimulation and shock therapy. To sense right atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have a right atrial ring electrode 23 to allow bipolar stimulation or sensing in combination with the right atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28. In an alternative embodiment, the coronary sinus lead 24 may also include a left ventricular ring electrode 25.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector having a plurality of terminals, 42, 44, 45, 46, 48, 52, 54, 56, and 58 (shown schematically and, for convenience, the names of the electrodes to which they are connected are shown next to the terminals). As such, to achieve right atrial sensing and stimulation, the connector includes at least a right atrial tip terminal ($A_R$ TIP) 42 adapted for connection to the atrial (AR) tip electrode 22. The connector may also include a right atrial ring terminal ($A_R$ RING) 43 for connection to the atrial ring electrode 23, and a left ventricular ring ($V_L$ RING) 45 for connection to the left ventricular ring electrode 25.

To achieve left chamber sensing, pacing, and shocking, the connector includes at least a left ventricular tip terminal ($V_L$ TIP) 44, a left atrial ring terminal ($A_L$ RING) 46, and a left atrial shocking coil terminal ($A_L$ COIL) 48, which are adapted for connection to the left ventricular tip electrode 26, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

Representative types of control circuitry that may be used with the present invention include the microprocessor-based control system of U.S. Pat. No. 4,940,052 to Mann et. al. For a more detailed description of the various timing intervals used within the stimulation device and their inter-relationship, reference is made to U.S. Pat. No. 4,788,980 (Mann et. al). Each of these references is incorporated by reference herein in its entirety.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via an electrode configuration switch 74. It is understood that to provide stimulation therapy in each of the four chambers of the heart, the atrial and ventricular pulse generators, 70 and 72, may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

It should be understood that the electrode configuration switch 74 illustrated in FIG. 2 may allow various electrode combinations to be used for stimulation and/or sensing. Thus, various configurations may be defined to implement the diagnostic feature described herein.

The microcontroller 60 further includes timing control circuitry 79, which is used to control the timing of such stimulation pulses (e.g., pacing rate, atrial-ventricular (AV) delay, atrial interconduction (A-A) delay, or ventricular interconduction (V-V) delay, etc.), as well as to keep track of the timing of refractory periods, blanking intervals, noise detection windows, evoked response detection windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches.

Atrial sensing circuits (ATR. SENSE) 82 and ventricular sensing circuits (VTR. SENSE) 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Stimulation during pacing may be performed in a bipolar mode in devices combining pacing and cardioversion/defibrillation functions because unipolar stimulation may interfere with arrhythmia detection. Hence, in one embodiment, the switch bank 74 is configured such that: right atrial pacing and sensing is performed in a bipolar fashion between the right atrial tip electrode 22 and right atrial ring electrode 23; right ventricular pacing and sensing is performed in a bipolar fashion between right ventricular tip electrode 32 and right ventricular ring electrode 34; and left ventricular pacing and sensing is performed in a bipolar fashion between coronary sinus tip electrode 26 and the coronary sinus ring electrode 27. Right ventricular sensing may alternatively be configured between the right ventricular coil electrode 36 and the right ventricular ring electrode 34. Bipolar sensing may also be achieved using an integrated bipolar lead wherein the right ventricular coil electrode 36 and right ventricular ring electrode 34 are electrically coupled within the right ventricular lead body 30. Bipolar sensing is then performed between the right ventricular tip electrode 32 and the coupled right ventricular coil electrode 36 and right ventricular ring electrode 34. Any electrode combination that allows acceptable stimulation and sensing thresholds may be used. By employing the right ventricular coil electrode 36, possibly in combination with right ventricular ring electrode 34, the electrode surface during sensing is increased, advantageously reducing the effects of lead polarization. Other techniques of reducing lead polarization such as titanium nitride coating may also be used to improve the operation.

Each sensing circuit, 82 and 84, preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 for triggering or inhibiting the atrial and ventricular pulse generators 70 and 72, respectively, in a demand fashion, in response to the absence or presence of cardiac activity in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 utilizes the atrial and ventricular sensing circuits 82 and 84 to sense cardiac signals for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.), to determine the type of remedial therapy that is needed (e.g., bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture." The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred. The implementation of an exemplary capture detection circuitry and algorithm is described, for example, in U.S. Pat. No. 4,969,467 to Callaghan et al., which is incorporated by reference herein in its entirety.

The microcontroller 60 is further coupled to a memory 94 by a suitable data/address bus 96, wherein the programmable operating parameters used by the microcontroller 60 are stored and modified, as required, to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy. A feature is the ability to sense and store a relatively large amount of data (e.g. from the data acquisition system 90), which data may then be used for subsequent analysis to guide the programming of the device. In a preferred embodiment, data resulting from periodic threshold tests are written to memory 94. The threshold measurement and the time and date at which it was made are stored in memory 94 so that changes in threshold over time may be graphically displayed on an external device 102, such as a programmer with an LCD display, after being downloaded via telemetry circuit 100 and communication link 104.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104. In a preferred embodiment, with a telemetry wand positioned over the stimulation device 10, an evoked response sensitivity test can be performed according to a control program located in external device 102, in this case a programmer. The methods of an evoked response sensitivity test will be described in detail in conjunction with FIG. 3.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various stimulation parameters (such as rate, AV Delay, V-V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 mu·A, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 that is enabled by the microcontroller 60 via a control signal 114.

In the case that it is a primary function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV coil electrode 36, or as part of a split electrical vector using the SVC coil electrode 38 or the left atrial coil electrode 28 (i.e., using the RV coil electrode 36 as a common electrode).

Cardioversion shocks are generally considered to be of low to moderate energy level (so as to minimize pain felt by the patient), and/or synchronized with an R-wave and pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
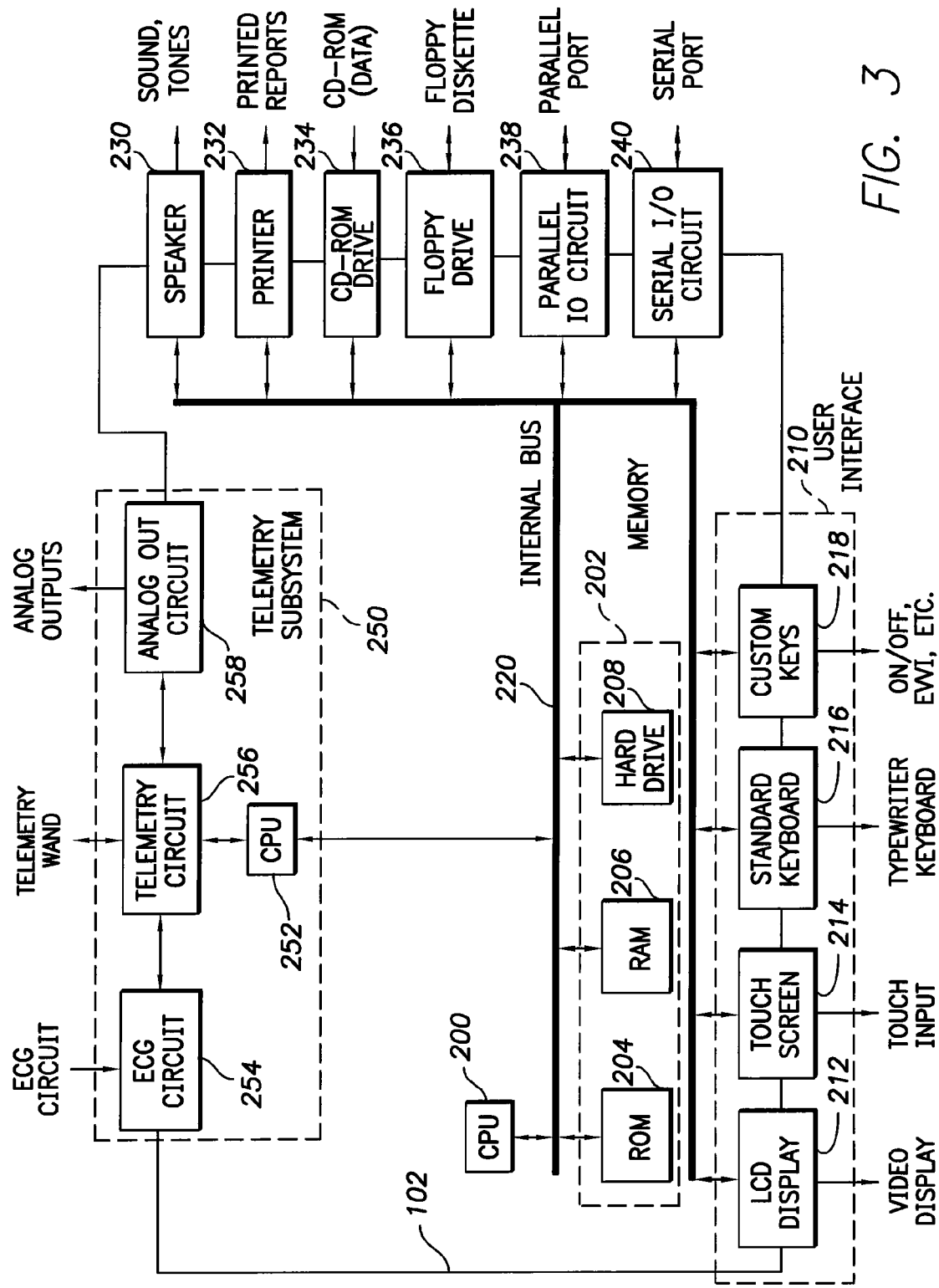
FIG. 3 is a block diagram illustrating the basic elements of an external device that may send and receive commands or data through telemetric communication with the implantable device of FIG. 2.

FIG. 3 illustrates a simplified block diagram of the external programming device 102 that communicates with device 10 through a telemetry circuit 100. The external device 102 includes a central processing unit (CPU) 200 that controls the operations carried out by the external device 102, such as programming the operating parameters of device 10 or carrying out various testing or diagnostic functions. Testing and diagnostic functions preferably include evoked response sensitivity testing, and may also include algorithms or methods for non-invasive programmed stimulation for arrhythmia induction, arrhythmia detection and termination testing, threshold testing, lead impedance measurements, etc.

CPU 200 is in communication with a memory (or data storage) 202 via an internal bus 220. The memory 202 may include a read-only memory (ROM) 204, a random access memory (RAM) 206, and hard drive 208. Operating parameters and algorithms controlling the programming and testing functions carried out by the external device 102 may be stored in memory 202 and accessed by CPU 200.

External device 102 is equipped with a user interface 210 that allows connection to an LCD display 212, a touch screen 214, a key board 216, and custom keys 218 that control a specific function or deliver a specific command automatically. Each component of the user interface 212 is also in communication with the CPU 200 and memory 202 via the internal bus 220 to allow user input, such as programming commands delivered using the touch screen 214, keyboard 216, or custom keys 218, to be received by the CPU 200 and/or stored in memory 202.

Programming selections made by a user and results of programming or testing operations may be displayed on the video display 212. Messages relating to the success of the programming command, recommended programmed settings, or warnings to the user regarding selected parameters may also be displayed on the video display 212.

The CPU 200 and memory 202 are also in communication with various input/output interfaces via the internal bus 220 that may include: a speaker 230 for delivering sounds or tones during the programming procedures; a printer 232 for printing results of programming or testing operations; a CD-ROM drive 234 and floppy drive 236 to which data from testing or programming operations may be written; and a parallel input/output port 238 and a serial input/output port 240 to allow connection to auxiliary equipment.

The external device 102 is further equipped with a telemetry subsystem 250. The telemetry subsystem 250 includes a central processing unit (CPU) 252 for controlling the transfer of data between the external device 102 and the implanted device 10. Thus, the telemetry CPU 252 is in communication with the internal bus 220 so that data may be transferred between the telemetry subsystem 250 the CPU 200, memory 202, user interface 210, and other input/output interfaces, 230, 232, 234, 236, 238, and 240.

The telemetry CPU 252 is connected to at least three interfaces which facilitate the receipt or transmission of data. An ECG circuit interface 254 allows connection to surface ECG leads for collecting a patient's ECG. The ECG may be displayed in real time on the video display 212. A telemetry circuit interface 256 allows connection to a telemetry wand that is placed over the implanted device 10 for receiving or sending data such as cardiac signal data stored in the memory 94 of device 10 or programmed operating parameters received at the user interface 210. An analog output circuit interface 258 allows connection to an analog output port to a remote printer or data recording system such as a hospital based electronic record.

As discussed above, a system that is configured to operate the device 10 to facilitate a medical procedure may be incorporated into the device 10, and may include the device itself. It should be understood however, that other configurations are possible, such as a system comprising the device 10 and elements external to the device 10. With respect to FIG. 2, the system is described as being incorporated into the device 10.

The microcontroller 60 or another processor (not shown) may be configured to monitor a plurality of parameters associated with the plurality of implanted leads 20, 24 and 30. It should be noted that such monitoring may be of the leads 20, 24 and 30 or of the various electrodes thereof.

For example, the device 10 may include a morphology detector 109 and/or other circuitry for lead monitoring, which may be included in the microcontroller 60 as modules, applications, routines, etc. Various techniques for monitoring leads and/or detecting the morphology of a signal are known, and may be incorporated in the morphology detector 109 or other circuitry. The details of the morphology detector 109 and other circuitry for lead monitoring is omitted for the sake of brevity.

In addition, the microcontroller 60 or another processor (not shown) may be configured to monitor for detectable characteristics associated with medical procedures, as discussed herein. In particular, the microcontroller 60 may include a monitoring circuit or module 111 configured to perform various operations of the methods described herein, either itself or in combination with other elements of the microcontroller 60. Although the monitoring circuit/module 111 is described herein as performing the monitoring/detecting operations, and the microcontroller 60 is described herein as performing most other operations, it should be understood that any suitable division of performance of operations is possible, particularly by implementation of discrete modules for individual operations/functions, although the microcontroller 60 may be suitably configured to perform nearly any operation/function itself or in combination with appropriate hardware and/or software as is well known in the electrical and computer arts. Further, the microcontroller 60 may perform its monitoring/detecting operations/functions employing one or more sensors or detectors as suitable for the particular characteristics to be monitored/detected. Such sensors or detectors may be those conventionally used for the particular characteristics, and thus are not discussed in detail herein.

As discussed above, the device 10 may include a telemetry circuit 100 that allows operating parameters to be input to program the device 10. Various operating parameters, including sets of operating parameters, may be received from the telemetry circuit 100 by the microcontroller 60 and stored in the memory 94. Based on a current configuration or conditions, a set of operating parameters may be accessed from the memory 94 and either supplied to the appropriate elements of the device 10 and/or applied to the software routines for controlling the elements and/or operations of the device 10. Thus, once programmed, the device 10 will have a current set of operating parameters prior to a medical procedure is to be performed.

Similarly, the telemetry circuit 100 and/or the external device 102 may provide a user interface for reprogramming the device with an interim or temporary operating parameter (s), inputting/selecting a medical procedure that is to be performed, inputting/selecting a detectable characteristic(s) for the medical procedure, as well as inputting/selecting any other variables such as periods of time.

The memory 94 or another storage element (not shown) of the device 10 may provide storage for as much or as little data as appropriate for a desired implementation. For example, in a substantially automated implementation, lists of medical procedures, corresponding interim operating parameters, corresponding detectable characteristics, and appropriate time values for the elapsed time, first period of time and second period of time may be stored. As discussed above, this may allow a user to interface with the device 10 by "pressing a button" to send a signal to the device 10 that indicates that a medical procedure is to be performed. In response, the microcontroller 60 may walk the user through a series of menus or lists that allow the user to select the medical procedure, and, as appropriate, the interim operating parameter(s), detectable characteristic(s), and/or time value(s) for the elapsed time, first period of time and/or second period of time. In a simplest case, selection of a medical procedure by the user may automatically determine all other settings as appropriate for that medical procedure. It should be understood, however, that any desired level of user interactivity and control of settings may be employed, as appropriate or desired.

Thus, in general, the microcontroller 60 may be configured to temporarily reprogram the device 10 to facilitate a medical procedure, to monitor one or more detectable characteristics associated with the medical procedure, and to resume normal programming of the device 10 based upon detection of the detectable characteristic(s). The system, as part of the microcontroller 60 or separate therefrom, may include any appropriate circuitry, sensors, modules and/or program code to monitor, detect and/or measure, etc. the detectable characteristics. By monitoring a detectable characteristic associated with the medical procedure, a suitable (safe) timing for reestablishing normal operation, i.e., normal programming, of the device 10 may be determined. Further, as discussed above, this may be accomplished without further involvement of a doctor or medical technician to perform reprogramming after the medical procedure is completed.

Figure 4:
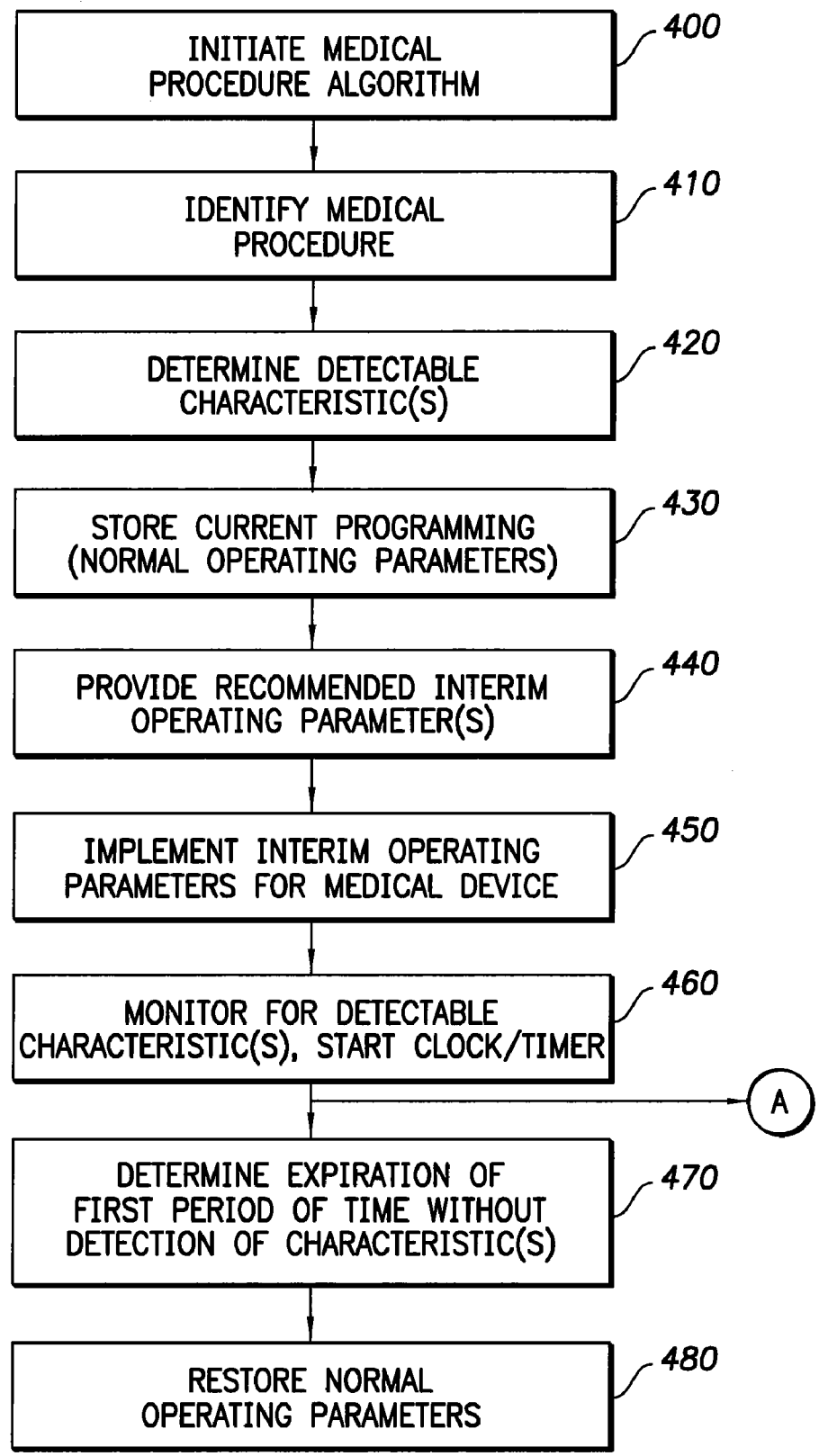
FIGS. 4 and 5 are process flow charts illustrating an overview of operations that may be included for operating the implantable device of FIG. 2 to facilitate a medical procedure.
Figure 5:
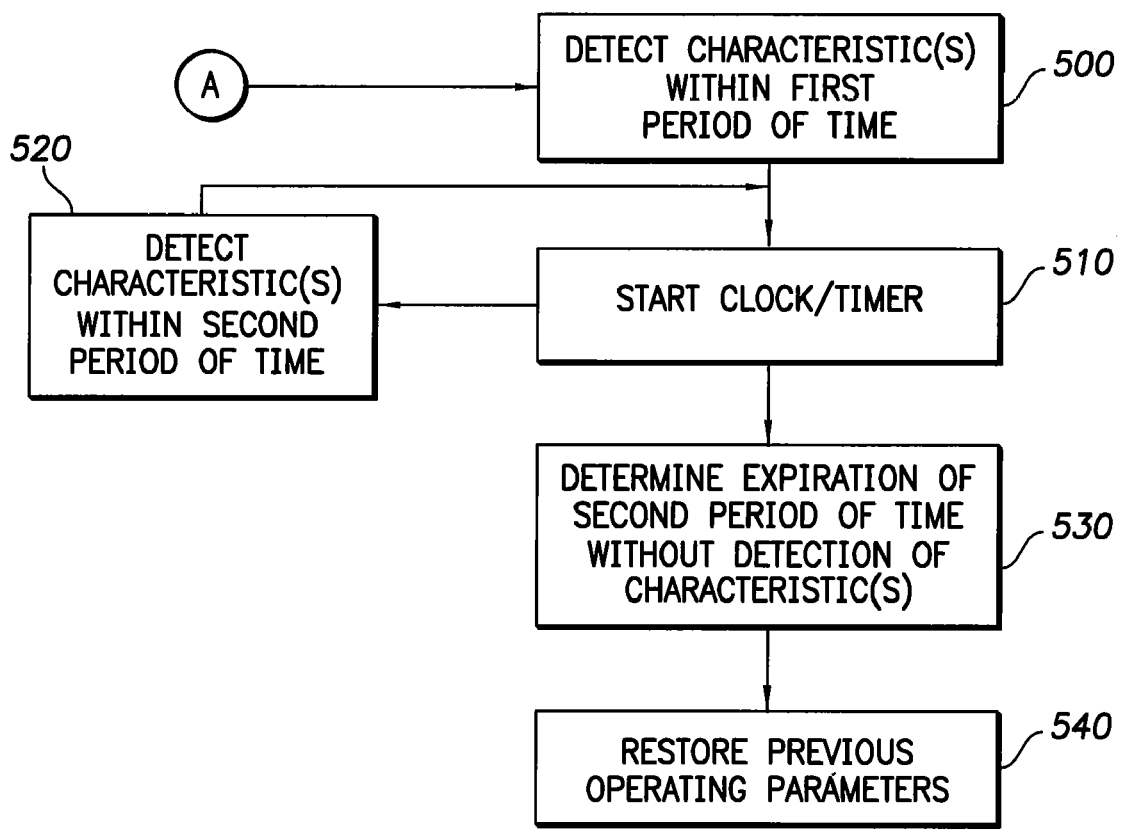
Figure 6:
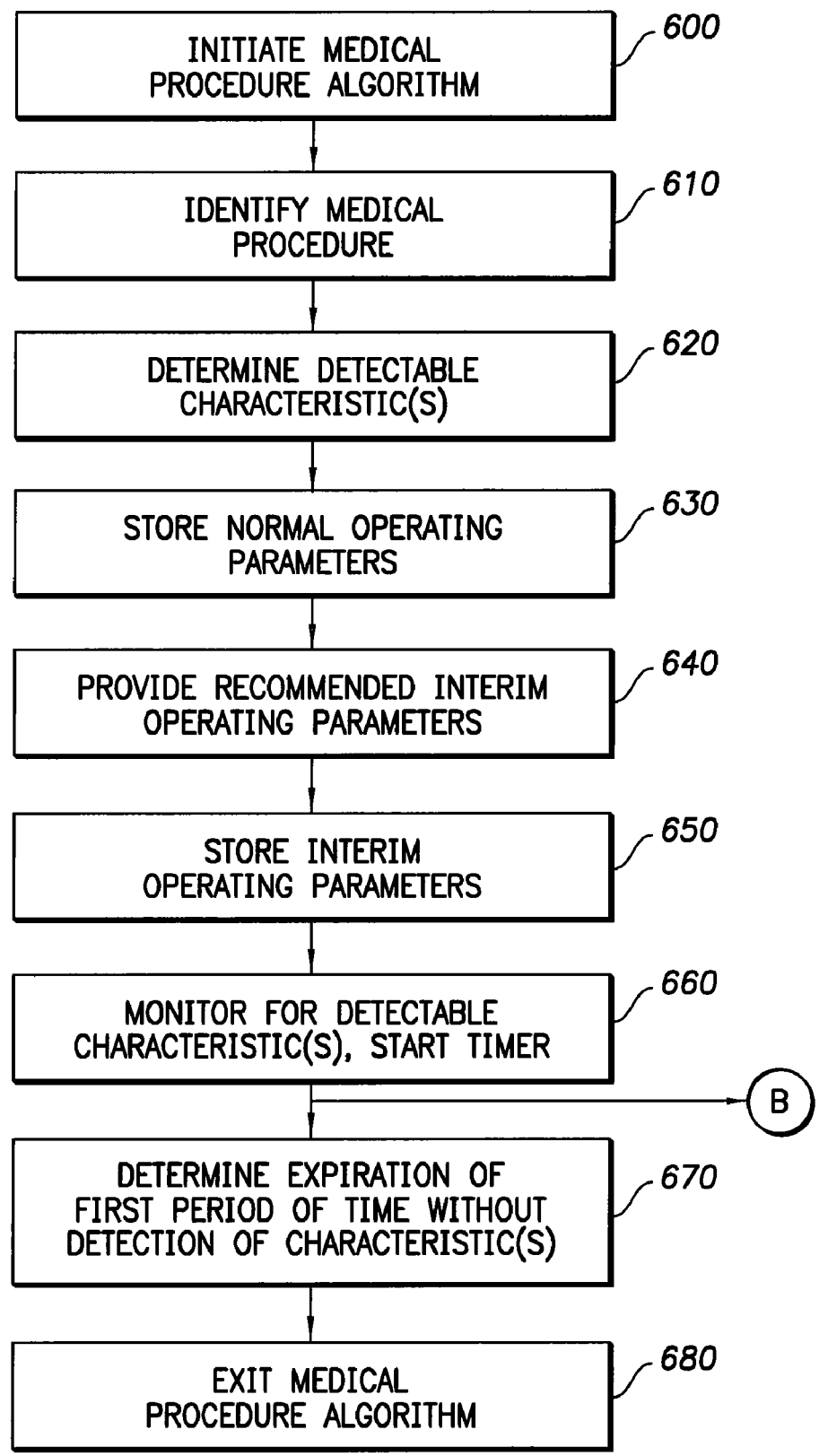
FIGS. 6 and 7 are process flow charts illustrating an overview of alternative operations that may be included for operating the implantable device of FIG. 2 to facilitate a medical procedure.
Figure 7:
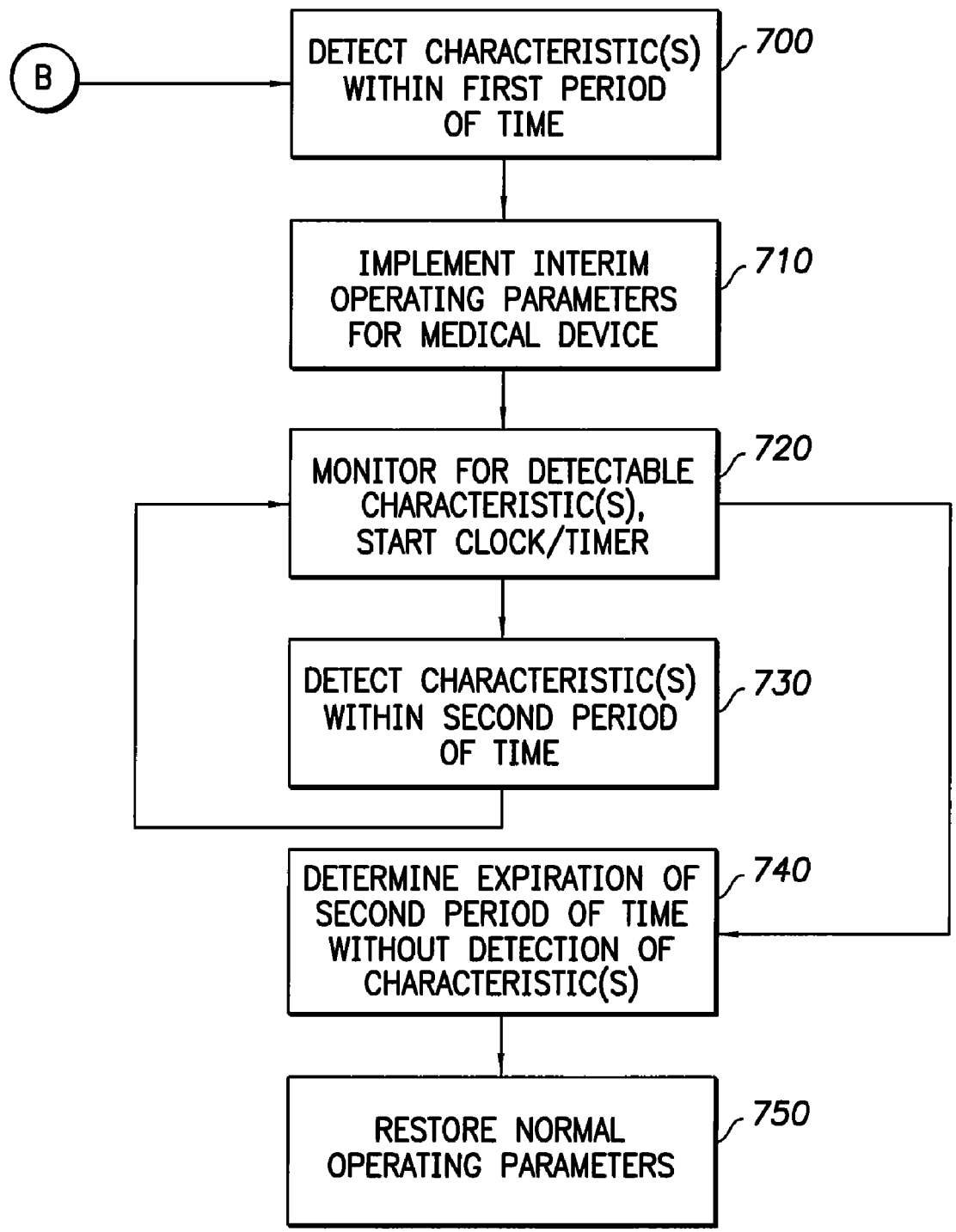

In FIGS. 4 and 5, flow charts are shown describing an overview of operations implemented in one embodiment of the implanted device 10 and external device 102. In FIGS. 6 and 7, flow charts are shown describing an overview of alternative operations. In these flow charts, the various algorithmic steps are summarized in individual "blocks". Such blocks describe specific actions or decisions that may be made or carried out as the algorithm proceeds. Where a microcontroller (a controller, or an equivalent device) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

It should be understood that the order of operations may be altered, that various operations may be optional and/or omitted, and that other operations may be employed, such as those described herein, to modify the embodiment represented by FIGS. 4 and 5 or the embodiment represented by FIGS. 6 and 7. As such, it should be understood that numerous implementations are possible beyond the particular process illustrated by these flow charts. It should be understood that suitable hardware and/or software may be included in the device or separate from the device to carry out the various operations described.

In FIG. 4, control may begin with the implantable medical device operating with normal programming, e.g., with a set of normal operating parameters that allows the device to behave normally, i.e., to provide its intended health benefits, e.g., treatment, therapy and/or monitoring for treatment, therapy, emergency, etc. When a patient having the medical device implanted is to be subjected to a medical procedure, a user, such as a doctor or medical technician, may "press a button" to initiate a medical procedure algorithm for the device [BLOCK 400]. It should be understood that the operation may involve a periodic routine that checks to see if a signal or command has been received, or the device may simply continue its normal operations unless a signal/command is received.

Once the medical procedure algorithm is initiated, the particular medical procedure to be performed on the patient may be identified [BLOCK 410]. The medical procedure may be identified in any suitable manner, such as by selection from a list of medical procedures anticipated to be encountered for which reprogramming of the device is appropriate or necessary, for example, to avoid undesired interaction with the device by the procedure. The algorithm may also allow the user to input other medical procedures not listed. In such case, the user may need to specify additional inputs, as discussed below. However, the system and/or the device may be configured to add the previously unlisted procedure to the list, along with any other specified inputs, for future reference.

Once the medical procedure has been identified, one or more detectable characteristics associated with the identified procedure may be determined [BLOCK 420]. This operation may be performed automatically, for example, by the system and/or the device having one or more preset characteristics for each medical procedure listed. For a medical procedure that is not listed, the system and/or the device may provide a list of options of characteristics for selection by the user. Such a list may include all characteristics for which the system is capable of monitoring or which the system is capable of detecting.

Next, the current programming, e.g., normal operating parameters, may be stored [BLOCK 430]. The parameters may be stored, for example, in internal memory of the device for easy recall once the medical procedure is complete. For a device that has multiple sets of operating parameters stored, this operation may involve storing an identification of the particular set as the current set of normal operating parameters rather than a duplicate storing of the current set of operating parameters.

The system and/or the device may provide recommended interim operating parameters for reprogramming the device to facilitate the medical procedure [BLOCK 440]. As discussed above, the recommended interim operating parameters may be based on the particular medical procedure identified. The system and/or device may provide one or more options as recommendations, for example, to provide different levels of safety, to account for different equipment to be used for the procedure, to account for different levels/settings/intensities to be used for the procedure, or other considerations The user may select a recommended set of interim operating parameters or may input modified interim operating parameters to reprogram the device for the medical procedure, that is, implement the interim operating parameters [BLOCK 450]. The ability of the user to vary from recommended interim parameters may be restricted based on the experience and/or the education of the particular user. For example, only a doctor may be permitted to vary from recommended interim parameters.

Once the interim operating parameters implemented, the system and/or the device may begin monitoring for the detectable characteristic(s), and a clock/timer may begin [BLOCK 460]. Although not shown for the sake of brevity, a first period of time may be set by the user, by selecting a default period, selecting a period from a list of recommended periods and/or inputting a variable period, to allow the first period of time to be adjusted for anticipated time to elapse between reprogramming and the start of the medical procedure. Alternatively, the first period of time may be preset to a particular value suitable for medical procedures generally. However, a preset time would not allow for flexibility, and would only provide a fixed safety margin, not allowing for any variance based, for example, on the condition of the patient. It should be understood that the time periods discussed herein may be set as a duration, such as hours and minutes, or may be set as a date and time, as appropriate or desired.

For example, the first period of time may expire without the system or the device detecting the detectable characteristic [BLOCK 470]. The lack of detecting the characteristic(s) within the first period of time, i.e., before the clock/timer runs down or times out, indicates that the medical procedure has not started within the first period of time. In response, the system may automatically restore the normal operating parameters previously stored [BLOCK 480], that is, the normal operating parameters existing at the time the medical procedure algorithm was initiated. Thus, if the medical procedure is not started within a desired period of time after the device is reprogrammed, the device will automatically be restored to its normal operating condition. This prevents the patient from being without the health benefits provided by the medical device for longer than the first time period, for example, should the medical procedure be delayed, postponed or even canceled.

The medical staff involved with the patient, including those overseeing the reprogramming of the device and the performance of the medical procedure on the patient, should be aware of the first period of time so as not to begin the medical procedure if the first period of time has expired. Thus, the first period of time should be monitored in some manner. One approach may be to provide a warning or alarm signal output by the system and/or the device that indicates that the first period of time has expired and that the reprogramming for the medical procedure is no longer in place or active on the device.

As shown by the continuation into the flow chart of FIG. 5, the system and/or the device alternatively may detect the detectable characteristic(s) within the first period of time [BLOCK 500]. The detection of the characteristic(s) within the first period of time, i.e., before the clock/timer runs down or times out, indicates that the medical procedure has started within the first period of time. In response, another clock/timer may begin [BLOCK 510].

Although not shown for the sake of brevity, a second period of time may be set by the user, by selecting from a list of recommended periods and/or inputting a variable period, to allow the second period of time to be adjusted for anticipated time to elapse to complete the medical procedure and provide a margin of safety before restoring the stored normal operating parameters to reestablish normal behavior and operation of the device.

Alternatively, the second period of time may be preset to a particular value suitable for medical procedures generally. In such case, the operation of monitoring for the detectable characteristic(s) may continue such that each detection of the characteristic(s) reinitiates or resets the clock/timer. That is, each detection of the detectable characteristic(s) within the second period of time [BLOCK 520] may return the process to the operation of starting the clock/timer [BLOCK 510]. Once the second period of time expires without another detection of the characteristic(s) [BLOCK 530], a signal or command may be generated to cause the stored normal operating parameters to automatically be restored [BLOCK 540], that is, to automatically reestablish the normal operating parameters existing at the time the medical procedure algorithm was initiated. Thus, once the medical procedure has been completed, as indicated by no further detection of the detectable characteristic(s) within the second period of time, the device will automatically be restored to its normal operating condition. This prevents the patient from being without the health benefits provided by the medical device for longer than the second time period after the medical procedure has been completed, even if a doctor or a medical technician is unavailable after the medical procedure is completed.

This does not prevent a doctor or a medical technician, for example, from restoring the device to its normal operating condition [BLOCK 540] prior to expiration of the second period of time. Thus, if the doctor or medical technician is available or present once the medical procedure is completed, the medical procedure algorithm may be overridden to restore the normal operating parameters at an earlier time, thus providing even greater benefit to the patient. For example, the doctor or medical technician may "press a button" to cancel the medical procedure algorithm and restore the normal operating parameters of the device or program other operating parameters as desired.

Turning to the alternative set of operations starting in FIG. 6, control may begin with the implantable medical device operating with normal programming as before. Similar to above, a user may initiate a medical procedure algorithm for the device [BLOCK 600], and then the particular medical procedure to be performed on the patient may be identified [BLOCK 610]. Then, as before, one or more detectable characteristics associated with the identified procedure may be determined [BLOCK 620]. Next, the current programming, e.g., normal operating parameters, may be stored [BLOCK 630].

Again, the system and/or the device may provide recommended interim operating parameters for reprogramming the device to facilitate the medical procedure [BLOCK 640]. As discussed above, the user may select a recommended set of interim operating parameters or may input modified interim operating parameters, which are then stored [BLOCK 650].

Once the interim operating parameters are stored, the system and/or the device may begin monitoring for the detectable characteristic(s), and a clock/timer may begin [BLOCK 660]. The first period of time may expire without the system or the device detecting the detectable characteristic [BLOCK 670]. The lack of detecting the characteristic(s) within the first period of time, i.e., before the clock/timer runs down or times out, indicates that the medical procedure has not started within the first period of time. In response, the system may automatically exit the medical procedure algorithm. The system may also provide some form of notification, warning or alarm signal to the patient, the doctor, the medical technician, or some other responsible party such as the medical staff involved with the patient, including those overseeing the reprogramming of the device and the performance of the medical procedure on the patient, to ensure that the medical procedure is not attempted once the first time period has expired.

As shown by the continuation into the flow chart of FIG. 7, the system and/or the device alternatively may detect the detectable characteristic(s) within the first period of time [BLOCK 700]. The detection of the characteristic(s) within the first period of time, i.e., before the clock/timer runs down or times out, indicates that the medical procedure has started within the first period of time. In response, the interim operating parameters may be implemented for the medical device [BLOCK 710]. Once the interim operating parameters are implemented, the system may continue or resume monitoring for the detectable characteristic(s) and another clock/timer may begin [BLOCK 720].

The operation of monitoring for the detectable characteristic(s) may continue such that each detection of the characteristic(s) reinitiates or resets the clock/timer. That is, each detection of the detectable characteristic(s) within the second period of time [BLOCK 730] may return the process to the operation of starting the clock/timer [BLOCK 720]. Once the second period of time expires without another detection of the characteristic(s) [BLOCK 740], a signal or command may be generated to cause the stored normal operating parameters to automatically be restored [BLOCK 750], that is, to automatically reestablish the normal operating parameters existing at the time the medical procedure algorithm was initiated. Thus, once the medical procedure has been completed, as indicated by no further detection of the detectable characteristic(s) within the second period of time, the device will automatically be restored to its normal operating condition.

Although the present invention has been described with reference to preferred embodiments, persons skilled in the art will recognize that changes may be made in form and detail without departing from the spirit and scope of the invention.

What is claimed is:

1. A method for operating a medical device for facilitating a medical procedure, the medical device implanted in a patient, the method comprising:
storing at least one current operating parameter of the device in a storage element of the device;
setting at least one interim operating parameter for the device;
monitoring for at least one detectable characteristic of a medical procedure to be performed on the patient; and
based upon completion of a time-out following the last detection of the at least one detectable characteristic, retrieving the at least one operating parameter from the storage element and replacing the at least one interim operating parameter with the retrieved at least one operating parameter.

2. The method of claim 1, further comprising determining the at least one detectable characteristic based on the medical procedure to be performed.

3. The method of claim 2, further comprising identifying the medical procedure to be performed to the device.

4. The method of claim 3, wherein the device automatically determines the at least one detectable characteristic to monitor based on the identified medical procedure.

5. The method of claim 3, wherein the device provides a list of medical procedures and identifying the medical procedure to be performed comprises selecting a procedure from the list.

6. The method of claim 5, wherein the device automatically determines the at least one detectable characteristic to monitor based on the selected procedure.

7. The method of claim 1, wherein the at least one interim operating parameter is set based on the medical procedure to be performed.

8. The method of claim 1, wherein the device automatically retrieves the at least one operating parameter from the storage element and replaces the at least one interim operating parameter with the retrieved at least one operating parameter based upon detection of the at least one detectable characteristic.

9. The method of claim 8, wherein retrieving the at least one operating parameter from the storage element and replacing the at least one interim operating parameter with the retrieved at least one operating parameter occurs at a predetermined elapsed time after detection of the at least one detectable characteristic.

10. The method of claim 9, wherein retrieving the at least one operating parameter from the storage element and replacing the at least one interim operating parameter with the retrieved at least one operating parameter occurs at the predetermined elapsed time after a last detection of the at least one detectable characteristic.

11. The method of claim 1, wherein the device performs the monitoring.

12. A method for operating a medical device for facilitating a medical procedure, the medical device implanted in a patient, the method comprising:

storing at least one current operating parameter of the device in a storage element of the device;

setting at least one interim operating parameter for the device;

setting a first period of time;

during the first set period of time, monitoring for at least one detectable characteristic of a medical procedure to be performed on the patient; and when the at least one detectable characteristic is not detected during the first set period of time, retrieving the at least one operating parameter from the storage element and replacing the at least one interim operating parameter with the retrieved at least one operating parameter.

13. The method of claim 12, further comprising:

setting a second period of time; and when the at least one detectable characteristic is detected during the first set period of time, retrieving the at least one operating parameter from the storage element and replacing the at least one interim operating parameter with the retrieved at least one operating parameter at the second set period of time after detection of the at least one detectable characteristic.

14. The method of claim 13, wherein when the at least one detectable characteristic is detected during the first set period of time, retrieving the at least one operating parameter from the storage element and replacing the at least one interim operating parameter with the retrieved at least one operating parameter at the second set period of time after a last detection of the at least one detectable characteristic.

15. A method for operating a medical device for facilitating a medical procedure, the medical device implanted in a patient, the method comprising:

altering at least one operating parameter of the device from a pre-procedure setting;

monitoring for at least one detectable characteristic of a medical procedure to be performed on the patient; and returning the at least one operating parameter to the pre-procedure setting at a predetermined elapsed time after a last detection of the at least one detectable characteristic.

16. The method of claim 15, further comprising identifying the medical procedure to be performed on the patient to the device.

17. The method of claim 16, wherein the at least one operating parameter is altered based on the identified medical procedure.

18. The method of claim 15, wherein the device automatically returns the at least one operating parameter to the pre-procedure setting based on detection of the at least one detectable characteristic.

19. The method of claim 18, wherein returning the at least one operating parameter to the pre-procedure setting occurs at a predetermined elapsed time after detection of the at least one detectable characteristic.

20. The method of claim 18, wherein returning the at least one operating parameter to the pre-procedure setting occurs at the predetermined elapsed time after a last detection of the at least one detectable characteristic.

* * * * *